(12) United States Patent
Kim

(10) Patent No.: US 6,515,176 B1
(45) Date of Patent: Feb. 4, 2003

(54) 6-ACYLAMINO-5-SUBSTITUTED-BENZOXAZOL-2-ONE COMPOUNDS AND METHOD FOR USING THEM

(75) Inventor: Chang-Kyu Kim, Pittsford, NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 10/011,907

(22) Filed: Dec. 3, 2001

(51) Int. Cl.⁷ .............................................. C07C 273/18
(52) U.S. Cl. ....................................................... 564/49
(58) Field of Search ............................ 564/49; 558/417

(56) References Cited

U.S. PATENT DOCUMENTS

| | | | |
|---|---|---|---|
| 4,579,813 A | 4/1986 | Aoki et al. | |
| 4,743,595 A | 5/1988 | Itoh et al. | |
| 5,962,198 A | 10/1999 | Lau et al. | |
| 6,201,125 B1 * | 3/2001 | Begley | 546/298 |

* cited by examiner

Primary Examiner—Joseph K. McKane
Assistant Examiner—Jennifer C. Murphy
(74) Attorney, Agent, or Firm—Arthur E. Kluegel

(57) ABSTRACT

Disclosed is a 6-acylamino-5-substituted-benzoxazol-2-one compound having the structural formula I:

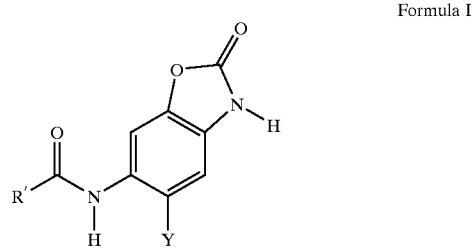

Formula I wherein
  Y is halogen or a substituent group linked to the rest of the compound by a hetero atom, and
  R' is a group containing at least 8 carbon atoms.
Also disclosed is a method for forming a cyan dye-forming coupler from the above compound. The method and intermediate provide a simplified manufacturing process.

11 Claims, No Drawings

6-ACYLAMINO-5-SUBSTITUTED-BENZOXAZOL-2-ONE COMPOUNDS AND METHOD FOR USING THEM

FIELD OF THE INVENTION

This invention relates to 6-acylamino-5-substituted-benzoxazol-2-one compounds and a method of using them to prepare cyan dye-forming couplers.

BACKGROUND OF THE INVENTION

Widely used cyan-dye forming couplers in color photography are 4-substituted-2,5-diaminophenol derivatives. Most of these couplers have been made from 4-halo-2-aminophenols as basic raw materials. Both amino and phenol groups are so reactive and sensitive that blocking both functional groups are required prior to introduction or manipulation of other substituents in the molecule. Formation of oxazole ring is the most commonly used for the blocking purpose. After the blocking, a nitro group is introduced at 6-position of benzoxazole (or 5-position of aminophenol ring) and 5-halo group of benzoxazole (or 4-halo group of aminophenol) is replaced, if necessary, with other groups by nucleophilic replacement reaction. The benzoxazole ring is then opened by hydrolysis, and a photographically useful group is placed on unblocked amine. Reduction of 5-nitro group gives 5-amino-2,4-disubstituted-phenol. Such an aminophenol is difficult to handle because of its reactivity and sensitivity and it is necessary to use it without isolation in the final step. The final step is usually a reaction between 5-amino group and a photographically useful ballasting acyl halide. Such a synthetic route using benzoxazole intermediates has been common and traditional in the synthesis of phenolic cyan couplers and well documented in the literature. Examples are U.S. Pat. No. 4,579,813; U.S. Pat. No. 4,743,595, JP60-091355; and M. Ono, et al, Heterocycles (1988), 27(4), 881-4.

Since 2-amino-4-chloro-5-nitrophenol has been commercially available in a bulk quantity, it has been used exclusively as a raw material in making 2-equivalent phenolic cyan couplers having a coupling-off group other than the halogen at 4-position. The phenolic OH group in the raw material is usually blocked by O-benzylation prior to replacement of 4-chlorine with other coupling-off group. A photographically useful functional group, typically a urea, is formed on unblocked amine. Reduction of 5-nitro group accomplishes deblocking at the same time to generate 5-amino-2,4-disubstituted-phenol. It is usually not isolated and used in the final ballasting reaction. This synthetic sequence starting from 2-amino-4-chloro-5-nitrophenol has been widely used in the preparation of 2-equivalent phenolic cyan couplers. Examples are U.S. Pat Nos. 4,775,616; 4,849,328, 4,923,791; 5,045,442; and 5,962,198.

A common feature of these two known synthetic routes is to form 'Urea First and Ballast Amide Last'. There are many significant disadvantages, however, in the preparation of 2-eq phenolic cyan couplers in that manner.

(1) Benzene ring of benzoxazoles is not activated for nitration so that a harsh reaction condition should be employed. For example, a large amount of concentrated sulfuric acid and a pre-formed nitronium ion mixture are usually used. Use of such a large amount of concentrated acid as a reaction medium make it difficult to handle during the reaction and to treat waste after the reaction. This is a disadvantage in safety, yield, and cost.

(2) Hydrolysis of oxazole ring is difficult. A polar solvent such as N,N-dimethyl formamide, N,N-dimethyl actamide, N-methyl pyrolidone, and dimethyl sulfoxide and a high temperature of over 100° C. are often required. Use of such a polar solvent is costly and environmentally unfavorable. Such a high temperature required for hydrolysis of benzoxazole containing a nitro group may impose a safety concern. This is a disadvantage in environment, safety, yield and cost.

(3) 2-Amino-4-halo-5-nitrophenol is thermally unstable as most of the low molecular weight aromatic nitro compounds are. Safety is a big issue in using such a thermally unstable compound. There are lots of limits for material usage and in reaction condition. This is a disadvantage in safety, yield, and cost.

(4) When 2-amino-4-chloro-5-nitrophenol is blocked by O-benzylation, 2-amino group is also benzylated although it is in some small extent. Presence of a small amount of impurity has a big impact on isolation and reduces the yield of product substantially. This is a disadvantage in yield and cost.

(5) Reaction of putting something on the amine at 2-position is difficult because of deactivation effect of the nitro group present at para position. It is usually required to employ either an activated reagent such as a carbamoyl chloride or an isocyanate, or a harsh condition such as a high boiling solvent and a high reaction temperature. Use of such an activated reagent may be costly and environmentally unfavorable. Necessity of employing such a harsh condition for a small molecule containing a nitro group may impose a safety concern. This is another disadvantage in environment, safety, yield and cost.

(6) Something put on the amine may cause other difficulties in the subsequent reduction step. For instances, if something put on the amine is an urea, its solubility may be limited and a polar solvent such as tetrahydrofuran or N,N-dimethylformamide that is costly and environmentally unfavorable may be necessary. If a group put on the amine contains a reducible substituent such as halogen, carbonyl, cyano, or nitro group, the subsequent reduction step is complicated and unwanted by-products or impurities may be generated. Generation of such by-products or impurities in the reduction has a big impact on the subsequent steps. Particularly, the reduced intermediate, an aminophenol derivative, is too sensitive to handle and it is necessary to be used in the final step without isolation. The final step of the synthetic sequence is a ballasting step. A ballasted compound is usually difficult to crystallize and purify. Presence of by-products or impurities makes it even worse. Such a difficult and unclean final step reaction hurts greatly the yield of final product. A drop in the yield of final step has a big impact on the cost of manufacturing the coupler. This is another disadvantage in yield and cost.

(7) All of the difficulties and limitations described above make the cost of manufacturing the coupler so high. It is a major reason why only a limited number of 2-equivalent phenolic cyan-dye forming couplers have been commercialized.

It is therefore desirable to develop a new intermediate and synthetic route that alleviates all the difficulties and limitations associated with the prior art and helps to simplify and reduce the cost of manufacturing phenolic cyan-dye forming couplers.

SUMMARY OF THE INVENTION

The present invention provides a 6-acylamino-5-substituted-benzoxazol-2-one compound having the structural formula I:

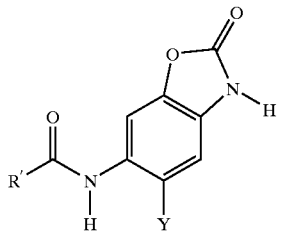

Formula I wherein
- Y is halogen or a substituent group linked to the rest of the compound by a hetero atom, and
- R' is a group containing at least 8 carbon atoms.

In another aspect this invention relates to a method of making a 2-equivalent phenolic cyan-dye forming coupler comprising the steps of:

(1) deblocking a compound of Formula I by hydrolysis of the benzoxazolone ring; and then, preferrably, (2) N-acylating the deblocked compound to append an R"CO group to the amine at the 2-position.

The invention also provides a method for using the compounds of Formula I as part of a simplified process for preparing a variety of 2-equivalent phenolic cyan-dye forming couplers.

DETAILED DESCRIPTION OF THE INVENTION

The present invention provides new intermediates and new synthetic method involving 'Ballast Amide First and Urea Last'. Advantages of making couplers with the new intermediates and the new synthetic method are multifold.

(1) A cyclic amide amine present at 3-position exerts an induction effect to activate 6-position of the benzoxazole ring. Therefore, nitration can be done cleanly using a dilute nitric acid in an environmentally favorable solvent such as water or acetic acid. This is an advantage in environment, safety, yield, and cost.

(2) Presence of a cyclic amide group also assists to reduce thermal instability of nitro compound prepared, which lessens a risk of unsafe handling and operation in subsequent steps. It is a significant advantage in the case of that a substituent like a halogen at 5-position is replaced with other coupling-off group (COG). It can only be done after the nitro group is introduced at 6-position. This is another advantage in environment, safety, yield, and cost.

(3) A nitro group is usually reduced by catalytic hydrogenation or hydrogen transfer reduction for economic and environmental reasons. When the nitro group in the intermediates is reduced, the cyclic amide is untouched. The aminophenol formed in this reduction is so clean and has no impurity or byproduct other than water. It therefore can be used without isolation in the next ballasting step. During these two-step processes, the cyclic amide unblocked has a significant role. It acts as a buffer to keep such a sensitive aminophenol intermediate from being complicated with a side reaction such as air oxidation or other deterioration. This is another advantage in environment, safety, yield and cost.

(4) The cyclic amide in an intermediate of invention does not affect the solubility of compound. The intermediates of invention can be used in the preparation of coupler using a low-cost and environmentally favorable solvent. This is another advantage in environment, safety, yield and cost.

(5) The 5-amino group is so reactive that it can be ballasted in the presence of water or alcohols, at a lower temperature, and in a short period of time. A clean ballasted-amine is obtained in a high yield. The presence of an N-acyl group offers yet another advantage. Its presence assists to make the ballasted compound more crystalline and easily isolable. This is an advantage in environment, yield and cost.

(6) Deblocking of the cyclic amide can be done typically by base induced hydrolysis. Obviously, the ballasted amine at 5-position is an N-acyl amine similar to cyclic amide. However, hydrolysis of cyclic amide can be done selectively without affecting the N-acyl at 5-position. It is because the ballast acyl group at 5-position is usually a bulky long chain alkyl or a short chain alkyl with a bulky α-substituent so that its steric bulkiness hinders hydrolytic cleavage of the amide. In addition, a coupling-off group at 4-position provides further steric hindrance. This is one of the key unobvious points of the present invention and another advantage in environment, safety, yield and cost.

(7) A deblocked 2-aminophenol derivative that is an immediate precursor of coupler can be obtained cleanly. Although it is still a sensitive aminophenol, its sensitivity is regulated by the presence of bulky ballast group in the molecule. The 2-amino group is yet so reactive that the final ballasting reaction can be done cleanly in a low cost environmentally favorable solvent at a low temperature and in a short period of time. This is another advantage in environment, yield and cost.

(8) All the advantages of the present invention described above alleviate almost all of the difficulties and limitations associated with the prior arts. Using the new intermediates and method of invention, every step of the process of making a coupler can be done safely in an environmentally favorable solvent, the minimum labor and burden cost, and the maximum yield and throughput. The present invention heretofore provides a method of manufacturing 2-equivalent phenolic cyan-dye forming couplers in a dramatically reduced cost.

The present invention provides new intermediates, 6-acylamino-5-substituted-benzoxazol-2-ones compounds, and a novel method for the preparation of intermediates for 2-equivalent phenolic cyan-dye forming couplers using them.

In the intermediate of Formula I, Y is a halogen or a substituent group linked to the rest of the compound by a hetero atom (atom other than carbon) and is desirably one of the coupling-off groups (COGs) known in the photographic art to be replaceable by oxidized color developing agent during photographic processing. Preferred Y groups include halogen, aryloxy, arylthio, arylsulfonyl, and heterocyclic. Preferred halogen is fluorine or chlorine. Preferred aryloxy group is phenoxy, 4-chlorophenoxy, 4-methylphenoxy, 4-methoxyphenoxy, 4-t-butylphenoxy, 4-t-pentylphenoxy, 2,4-di-t-butylphenoxy, or 2,4-di-t-pentyl-phenoxy. Preferred arylthio group is phenylthio, 4-methylphenylthio, 4-chlorophenylthio, or 4-methanesulfonylaminophenylthio. Preferred arylsulfonyl group is phenylsulfonyl, p-toluenesulfonyl, 4-chlorophenylsulfonyl, or 4-methanesulfonylaminophenylsulfonyl. Preferred heterocyclic group is 1-imidazolyl, 1-pyrazolyl, 3-N-ethylhydantoin-1-yl, 3-N-phenylhydantoin-1-yl, or 5,5-dimethyloxazolidine-2,4-dione-3-yl.

In the intermediate of Formula I, the group defined by R' is suitably a ballast group that is an organic radical of such size and configuration as to confer on the coupler molecule sufficient bulk to render the coupler substantially non-diffusible from the layer in which it is coated in a photographic element. Representative R' groups include substituted or unsubstituted alkyl or aryl groups containing a total of 8–30 carbon atoms. Representative substituents include alkyl, aryl, heteroaryl, alkoxy, aryloxy, alkylthio, arylthio, halogen, alkoxycarbonyl, aryloxycarbonyl, acyl, acyloxy, carbonamido, carbamoyl, alkylsulfonyl, arylsulfonyl, sulfonamido, and sulfamoyl groups where in the alkyl and aryl substituents, and the alkyl and aryl portions of the alkoxy, aryloxy, alkylthio, arylthio, alkoxycarbonyl, aryloxycarbonyl, acyl, acyloxy, carbonamido, carbamoyl, alkylsulfonyl, arylsulfonyl, sulfonamido, and sulfamoyl substituents contain 1–30 carbon atoms and 6–30 carbon atoms, respectively, and can be further substituted with such substituents. Preferred R' groups are 1-(2,4-di-t-pentylphenoxy)propyl, 1-(2,4-di-t-pentylphenoxy)pentyl, 1-(3-pentadecylphenoxy)propyl, 1-dodecylsulfonylpropyl, 1-dodecylsulfonylpentyl, 1-dodecylsulfonyl-2-methypropyl, 1-tetradecylsulfonylpropyl, 1-hexadecylsulfonylpropyl, 1-(4-butylsulfonylamino.

Scheme I

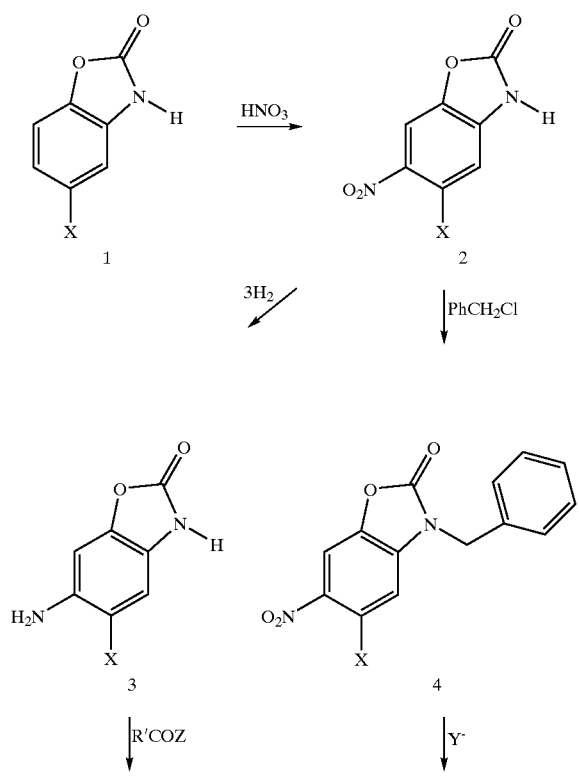

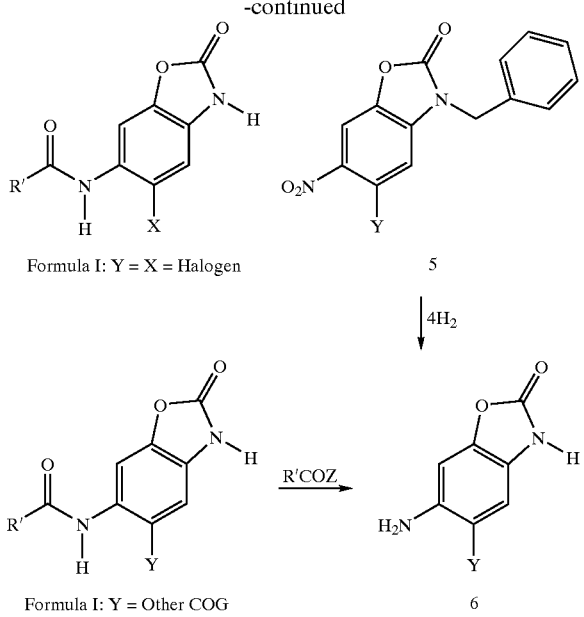

phenoxy)tridecyl, 1-(4-dodecyloxybenzenesulfonyl)propyl, and 1-(4-hexadecyloxy-benzenesulfonyl)propyl.

The preparation of the new intermediates of invention is shown in Scheme I. Nitration of a 5-halobenzoxazol-2-one (1) with commercial concentrated (70%) nitric acid gives a 5-halo-6-nitrobenzoxazol-2-one (2). Reduction of nitro group in the compound 2 by catalytic hydrogenation or hydrogen transfer reduction followed by N-acylation reaction with a ballasting agent defined by general formula R'COZ gives the desired intermediate of Formula I wherein Y is a halogen. The group defined by R' is same as defined above. The group defined by Z is one commonly known as a leaving group. Preferred Z groups include —OCOR, chloro, phenoxy, methanesulfonyloxy, ethoxycarbonyloxy, phenoxycarbonyloxy, and imidazolyl. For the case of the coupling-off group (Y) other than halogen, a cyclic amide amine (—CONH—) is further blocked by benzylation and the halogen is replaced by nucleophelic replacement reaction with an anion of coupling-off group (Y⁻) to give a 3-N-benzyl-6-nitro-5-substituted-benzoxazol-2-one (5). Reduction of the nitro group and debenzylation is done by catalytic hydrogenation or hydrogen transfer reduction. N-Acylation of the amine in the compound 6 with a ballasting agent R'COZ gives the desired intermediate of Formula I.

Scheme II illustrates a new method for the preparation of 2-equivalent phenolic cyan-dye forming couplers of color photography using the intermediate of the invention. The new method comprises the following two steps:

(1) Deblocking of cyclic amide in the intermediate of Formula I is done by base induced hydrolysis. The ballasted amine is so stable that a strong base and a harsh condition can be employed. The selective hydrolysis can be done preferably using a strong base such as sodium hydroxide, potassium hydroxide, or calcium hydroxide; in a high boiling hydrocarbon solvent such as toluene or xylene with a high boiling alcohol such as butanol or ethylene glycol as a co-solvent; at a high temperature from 100° C. to 200° C.; and at a short period of time from 1 to 6 hours.

Scheme II

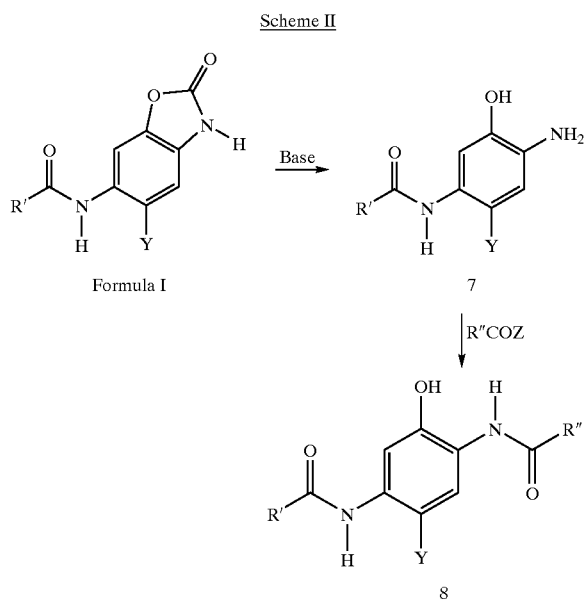

Formula I (2) The final step is a selective acylation of the unblocked amine derivative 7 with an acylating agent defined by general formula R"COZ. The group defined by R" is a photographically useful group that affects reactivity, sensitivity, and/or stability of the coupler 8 or hue and other spectral properties of the dye formed from the coupler. Representative R" groups include alkyl, haloalkyl, aryl, heteroaryl, arylamino, and heteroarylamino. Each aryl or heteroaryl portion has no substituent or 1 to 5, typically 1 to 2, substituent(s) of the same or different from each other. Representative substituents include, alkyl, aryl, heteroaryl, halogen, cyano, alkoxycarbonyl, aryloxycarbonyl, alkylcarbonyl, arylcarbonyl, heteroaryl-carbonyl, alkylsulfonyl, arylsulfonyl, heteroarysulfonyl, and the like. The group defined by Z is one commonly known as a leaving group. Representative Z groups include halogen, alkoxy, aryloxy, alkylsulfonyloxy, arylsulfonyloxy, alkoxycarbonyloxy, aryloxycarbonyloxy, and heteroaryl. Preferred Z groups are chloro, phenoxy, methanesulfonyloxy, ethoxycarbonyloxy, phenoxycarbonyloxy, and imidazolyl. Final acylation is preferably done in an aprotic solvent such as heptane, toluene, ethyl acetate, propyl acetate, or acetonitrile at a lower temperature from −10° C. to 40° C. and in a short period of time from 15 minutes to 4 hours. The reaction requires a weak organic or inorganic base to scavenge the byproduct HZ. Preferred week organic base is pyridine, 4-N,N-dimethylamino-pyridine, 2,6-lutidine, or imidazole. Preferred weak inorganic base is sodium acetate, potassium acetate, ammonium acetate, sodium bicarbonate, potassium bicarbonate, sodium carbonate, potassium carbonate, or ammonium carbonate. When R" is an arylamino or heteroaryl amino, an isocyanate of general formula R"NCO may be used instead of R"COZ with no base.

Unless otherwise specifically stated, use of the term "group", "substituted" or "substituent" means any group or atom other than hydrogen. Additionally, when reference is made in this application to a compound or group that contains a substitutable hydrogen, it is also intended to encompass not only the unsubstituted form, but also its form further substituted with any substituent group or groups as herein mentioned, so long as the substituent does not destroy properties necessary for the intended utility. Suitably, a substituent group may be halogen or may be bonded to the remainder of the molecule by an atom of carbon, silicon, oxygen, nitrogen, phosphorous, or sulfur. The substituent may be, for example, halogen, such as chlorine, bromine or fluorine; nitro, hydroxyl; cyano; carboxyl; or groups which may be further substituted, such as alkyl, including straight or branched chain or cyclic alkyl, such as methyl, trifluoromethyl, ethyl, t-butyl, 3-(2,4-di-t-pentylphenoxy) propyl, cyclohexyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy) ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentyl-phenoxy)acetamido, alpha-(2,4-di-t-pentylphenoxy) butyramido, alpha-(3-pentadecylphenoxy)-hexanamido, alpha-(4-hydroxy-3-t-butylphenoxy)-tetradecanamindo, 2-oxo-pyrrolidin- 1-yl, 2-oxo-5-tetradecylpyrrolin-1-yl, N-methyltetradecanamido, N-succinimido, N-phthalimido, 2,5-dioxo- 1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl) carbonylamino, p-dodecyl-phenylcarbonylamino,p-tolylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-tolylureido, N-(m-hexadecylphenyl)ureido, N-(2,5-di-t-pentylphenyl)-N'-ethylureido, and t-butylcarbonamido; sulfonamido, such as methylsulfonamido, benzenesulfonamido, p-tolylsulfonamido, p-dodecylbenzenesulfonamido, N-methyltetradecylsulfonamido, N,N-dipropyl-sulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl; N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethyihexylsulfonyl, dodecylsulfonyl, hexadecylsulfonyl, phenylsulfonyl, 4-nonylphenylsulfonyl, and p-tolylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-tolylsulfinyl; thio, such as ethylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1 (N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quatemary ammonium, such as triethylammonium; and silyloxy, such as trimethylsilyloxy.

If desired, the substituents may themselves be further substituted one or more times with.the described substituent groups. The particular substituents used may be selected by those skilled in the art to attain the desired photographic properties for a specific application and can include, for example, hydrophobic groups, solubilizing groups, blocking groups, and releasing or releasable groups. When a molecule may have two or more substituents, the substituents may be joined together to form a ring such as a fused ring unless otherwise provided. Generally, the above groups and substituents thereof may include those having up to 48 carbon atoms, typically 1 to 36 carbon atoms and usually less than 24 carbon atoms, but greater numbers are possible depending on the particular substituents selected.

The couplers made with the method of the invention can be used in any of the ways and in any of the combinations known in the art. Typically, the invention materials are incorporated in a melt and coated as a layer described herein on a support to form part of a photographic element. When the term "associated" is employed, it signifies that a reactive compound is in or adjacent to a specified layer where, during processing, it is capable of reacting with other components.

To control the migration of various components, it may be desirable to include a high molecular weight hydrophobe or "ballast" group in coupler molecules. Representative ballast groups include substituted or unsubstituted alkyl or aryl groups containing 8 to 48 carbon atoms. Representative substituents on such groups include alkyl, aryl, alkoxy, aryloxy, alkylthio, hydroxy, halogen, alkoxycarbonyl, aryloxcarbonyl, carboxy, acyl, acyloxy, amino, anilino, carbonamido, carbamoyl, alkylsulfonyl, arylsulfonyl, sulfonamido, and sulfamoyl groups wherein the substituents typically contain 1 to 42 carbon atoms. Such substituents can also be further substituted.

The photographic elements can be single color elements or multicolor elements. Multicolor elements contain image dye-forming units sensitive to each of the three primary regions of the spectrum. Each unit can comprise a single emulsion layer or multiple emulsion layers sensitive to a given region of the spectrum. The layers of the element, including the layers of the image-forming units, can be arranged in various orders as known in the art. In an alternative format, the emulsions sensitive to each of the three primary regions of the spectrum can be disposed as a single segmented layer.

A typical multicolor photographic element comprises a support bearing a cyan dye image-forming unit comprised of at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler, and a yellow dye image-forming unit comprising at least one blue-sensitive silver halide emulsion layer having associated therewith at least one yellow dye-forming coupler. The element can contain additional layers, such as filter layers, interlayers, overcoat layers, and subbing layers.

If desired, the photographic element can be used in conjunction with an applied magnetic layer as described in *Research Disclosure*, November 1992, Item 34390 published by Kenneth Mason Publications, Ltd., Dudley Annex, 12a North Street, Emsworth, Hampshire P010 7DQ, ENGLAND, and as described in Hatsumi Kyoukai Koukai Gihou No. 94-6023, published Mar. 15, 1994, available from the Japanese Patent Office. When it is desired to employ the inventive materials in a small format film, *Research Disclosure*, June 1994, Item 36230, provides suitable embodiments.

In the following discussion of suitable materials for use in the emulsions and elements of this invention, reference will be made to *Research Disclosure*, September 1996, Item 38957, available as described above, which is referred to herein by the term "Research Disclosure". The Sections hereinafter referred to are Sections of the Research Disclosure.

Except as provided, the silver halide emulsion containing elements employed in this invention can be either negative-working or positive-working as indicated by the type of processing instructions (i.e. color negative, reversal, or direct positive processing) provided with the element. Suitable emulsions and their preparation as well as methods of chemical and spectral sensitization are described in Sections I through V. Various additives such as UV dyes, brighteners, antifoggants, stabilizers, light absorbing and scattering materials, and physical property modifying addenda such as hardeners, coating aids, plasticizers, lubricants and matting agents are described, for example, in Sections II and VI through VIII. Color materials are described in Sections X through XIII. Suitable methods for incorporating couplers and dyes, including dispersions in organic solvents, are described in Section X(E). Scan facilitating is described in Section XIV. Supports, exposure, development systems, and processing methods and agents are described in Sections XV to XX. The information contained in the September 1994 *Research Disclosure*, Item No. 36544 referenced above, is updated in the September 1996 *Research Disclosure*, Item No. 38957. Certain desirable photographic elements and processing steps, including those useful in conjunction with color reflective prints, are described in *Research Disclosure*, Item 37038, February 1995.

Coupling-off groups are well known in the art. Such groups can determine the chemical equivalency of a coupler, i.e., whether it is a 2-equivalent or a 4-equivalent coupler, or modify the reactivity of the coupler. Such groups can advantageously affect the layer in which the coupler is coated, or other layers in the photographic recording material, by performing, after release from the coupler, functions such as dye formation, dye hue adjustment, development acceleration or inhibition, bleach acceleration or inhibition, electron transfer facilitation, and color correction.

The presence of hydrogen at the coupling site provides a 4-equivalent coupler, and the presence of another coupling-off group usually provides a 2-equivalent coupler. Representative classes of such coupling-off groups include, for example, chloro, alkoxy, aryloxy, hetero-oxy, sulfonyloxy, acyloxy, acyl, heterocyclyl, sulfonamido, mercaptotetrazole, benzothiazole, mercaptopropionic acid, phosphonyloxy, arylthio, and arylazo. These coupling-off groups are described in the art, for example, in U.S. Pat. Nos. 2,455,169, 3,227,551, 3,432,521, 3,476,563, 3,617,291, 3,880,661, 4,052,212 and 4,134,766; and in UK. Patents and published application Nos. 1,466,728, 1,531,927, 1,533,039, 2,006,755A and 2,017,704A.

Image dye-forming couplers may be included in the element such as couplers that form cyan dyes upon reaction with oxidized color developing agents which are described in such representative patents and publications as: "Farbkuppler-eine Literature Ubersicht," published in Agfa Mitteilungen, Band III, pp. 156–175 (1961) as well as in U.S. Pat. Nos. 2,367,531; 2,423,730, 2,474,293; 2,772,162; 2,895,826; 3,002,836; 3,034,892; 3,041,236; 4,333,999; 4,746,602; 4,753,871; 4,770,988; 4,775,616; 4,818,667; 4,818,672; 4,822,729; 4,839,267; 4,840,883; 4,849,328; 4,865,961; 4,873,183; 4,883,746; 4,900,656; 4,904,575; 4,916,051; 4,921,783; 4,923,791; 4,950,585; 4,971,898; 4,990,436; 4,996,139; 5,008,180; 5,015,565; 5,011,765; 5,011,766; 5,017,467; 5,045,442; 5,051,347; 5,061,613; 5,071,737; 5,075,207; 5,091,297; 5,094,938; 5,104,783; 5,178,993; 5,813,729; 5,187,057; 5,192,651; 5,200,305 5,202,224; 5,206,130; 5,208,141; 5,210,011; 5,215,871; 5,223,386; 5,227,287; 5,256,526; 5,258,270; 5,272,051; 5,306,610; 5,326,682; 5,366,856; 5,378,596; 5,380,638; 5,382,502; 5,384,236; 5,397,691; 5,415,990; 5,434,034; 5,441,863; EPO 0 246 616; EPO 0 250 201; EPO 0 271 323; EPO 0 295 632; EPO 0 307 927; EPO 0 333 185; EPO 0 378 898; EPO 0 389 817; EPO 0 487 111; EPO 0 488 248; EPO 0 539 034; EPO 0 545 300; EPO 0 556 700; EPO 0 556 777; EPO 0 556 858; EPO 0 569 979; EPO 0 608 133; EPO 0 636 936; EPO 0 651 286; EPO 0 690 344; German OLS 4,026,903; German OLS 3,624,777 and German OLS 3,823,049. Typically such couplers are phenols, naphthols, or pyrazoloazoles.

Couplers that form magenta dyes upon reaction with oxidized color developing agent are described in such representative patents and publications as: "Farbkuppler-eine Literature Ubersicht," published in Agfa Mitteilungen, Band III, pp. 126–156 (1961) as well as U.S. Pat. Nos. 2,311,082 and 2,369,489; 2,343,701; 2,600,788; 2,908,573; 3,062,653; 3,152,896; 3,519,429; 3,758,309; 3,935,015; 4,540,654; 4,745,052; 4,762,775; 4,791,052; 4,812,576; 4,835,094; 4,840,877; 4,845,022; 4,853,319; 4,868,099; 4,865,960; 4,871,652; 4,876,182; 4,892,805; 4,900,657; 4,910,124; 4,914,013; 4,921,968; 4,929,540; 4,933,465; 4,942,116; 4,942,117; 4,942,118; U.S. Pat. Nos. 4,959,480; 4,968,594; 4,988,614; 4,992,361; 5,002,864; 5,021,325; 5,066,575; 5,068,171; 5,071,739; 5,100,772; 5,110,942; 5,116,990; 5,118,812; 5,134,059; 5,155,016; 5,183,728; 5,234,805; 5,235,058; 5,250,400; 5,254,446; 5,262,292; 5,300,407; 5,302,496; 5,336,593; 5,350,667; 5,395,968; 5,354,826; 5,358,829; 5,368,998; 5,378,587; 5,409,808; 5,411,841; 5,418,123; 5,424,179; EPO 0 257 854; EPO 0 284 240; EPO 0 341 204; EPO 347,235; EPO 365,252; EPO 0 422 595; EPO 0 428 899; EPO 0 428 902; EPO 0 459 331; EPO 0 467 327; EPO 0 476 949; EPO 0 487 081; EPO 0 489 333; EPO 0 512 304; EPO 0 515 128; EPO 0 534 703; EPO 0 554 778; EPO 0 558 145; EPO 0 571 959; EPO 0 583 832; EPO 0 583 834; EPO 0 584 793; EPO 0 602 748; EPO 0 602 749; EPO 0 605 918; EPO 0 622 672; EPO 0 622 673; EPO 0 629 912; EPO 0 646 841, EPO 0 656 561, EPO 0 660 177; EPO 0 686 872; WO 90/10253; WO 92/09010; WO 92/10788; WO 92/12464; WO 93/01523; WO 93/02392; WO 93/02393; WO 93/07534; UK Application 2,244,053; Japanese Application 03192–350; German OLS 3,624,103; Germnan OLS 3,912,265; and German OLS 40 08 067. Typically such couplers are pyrazolones, pyrazoloazoles, or pyrazolobenzimidazoles that form magenta dyes upon reaction with oxidized color developing agents.

Couplers that form yellow dyes upon reaction with oxidized color developing agent are described in such representative patents and publications as: "Farbkuppler-eine Literature Ubersicht," published in Agfa Mitteilungen; Band III, pp. 112–126 (1961); as well as U.S. Pat. Nos. 2,298,443; 2,407,210; 2,875,057; 3,048,194; 3,265,506; 3,447,928; 4,022,620; 4,443,536; 4,758,501; 4,791,050; 4,824,771; 4,824,773; 4,855,222; 4,978,605; 4,992,360; 4,994,361; 5,021,333; 5,053,325; 5,066,574; 5,066,576; 5,100,773; 5,118,599; 5,143,823; 5,187,055; 5,190,848; 5,213,958; 5,215,877; 5,215,878; 5,217,857; 5,219,716; 5,238,803; 5,283,166; 5,294,531; 5,306,609; 5,328,818; 5,336,591; 5,338,654; 5,358,835; 5,358,838; 5,360,713; 5,362,617; 5,382,506; 5,389,504; 5,399,474;. 5,405,737; 5,411,848; 5,427,898; EPO 0 327 976; EPO 0 296 793; EPO 0 365 282; EPO 0 379 309; EPO 0 415 375; EPO 0 437 818; EPO 0 447 969; EPO 0 542 463; EPO 0 568 037; EPO 0 568 196; EPO 0 568 777; EPO 0 570 006; EPO 0 573 761; EPO 0 608 956; EPO 0 608 957; and EPO 0 628 865. Such couplers are typically open chain ketomethylene compounds.

Couplers that form colorless products upon reaction with oxidized color developing agent are described in such representative patents as: UK. 861,138; U.S. Pat. Nos. 3,632,345; 3,928,041; 3,958,993 and 3,961,959. Typically such couplers are cyclic carbonyl containing compounds that form colorless products on reaction with an oxidized color developing agent.

Couplers that form black dyes upon reaction with oxidized color developing agent are described in such representative patents as U.S. Pat. Nos. 1,939,231; 2,181,944; 2,333,106; and 4,126,461, German OLS No. 2,644,194 and German OLS No. 2,650,764. Typically, such couplers are resorcinols or m-aminophenols that form black or neutral products on reaction with oxidized color developing agent.

In addition to the foregoing, so-called "universal" or "washout" couplers may be employed. These couplers do not contribute to image dye-formation. Thus, for example, a naphthol having an unsubstituted carbamoyl or one substituted with a low molecular weight substituent at the 2- or 3-position may be employed. Couplers of this type are described, for example, in U.S. Pat. Nos. 5,026,628, 5,151,343, and 5,234,800.

It may be useful to use a combination of couplers any of which may contain known ballasts or coupling-off groups such as those described in U.S. Pat. No. 4,301,235; U.S. Pat. No. 4,853,319 and U.S. Pat. No. 4,351,897. The coupler may contain solubilizing groups such as described in U.S. Pat. No. 4,482,629. The coupler may also be used in association with "wrong" colored couplers (e.g. to adjust levels of interlayer correction) and, in color negative applications, with masking couplers such as those described in EP 213.490; Japanese Published Application 58-172,647; U.S. Pat. Nos. 2,983,608; 4,070,191; and 4,273,861; German Applications DE 2,706,117 and DE 2,643,965, UK. Patent 1,530,272; and Japanese Application 58-113935. The masking couplers may be shifted or blocked, if desired.

Typically, couplers are incorporated in a silver halide emulsion layer in a mole ratio to silver of 0.05 to 1.0 and generally 0.1 to 0.5. Usually the couplers are dispersed in a high-boiling organic solvent in a weight ratio of solvent to coupler of 1.0 to 10.0 and typically 1.0 to 2.0 although dispersions using no permanent coupler solvent are sometimes employed.

The invention may be used in association with materials that release Photographically Useful Groups (PUGS) that accelerate or otherwise modify the processing steps e.g. of bleaching or fixing to improve the quality of the image. Bleach accelerator releasing couplers such as those described in EP 193,389; EP 301,477; U.S. Pat. No. 4,163, 669; U.S. Pat. No. 4,865,956; and U.S. Pat. No. 4,923,784, may be useful. Also contemplated is use in association with nucleating agents, development accelerators or their precursors (UK Patent 2,097,140; UK. Patent 2,131,188); electrontransferagents (U.S. Pat. No. 4,859,578; U.S. Pat. No. 4,912,025); antifogging and anti color-mixing agents such as derivatives of hydroquinones, aminophenols, amines, gallic acid; catechol; ascorbic acid; hydrazides; sulfonamidophenols; and non color-forming couplers.

The couplers of the invention may further be used in combination with image-modifying compounds that release PUGS such as "Developer Inhibitor-Releasing" compounds (DIR's). DIR's useful in conjunction with the invention are known in the art and examples are described in U.S. Pat. Nos. 3,137,578; 3,148,022; 3,148,062; 3,227,554; 3,384, 657; 3,379,529; 3,615,506, 3,617,291; 3,620,746; 3,701, 783; 3,733,201; 4,049,455; 4,095,984; 4,126,459; 4,149, 886; 4,150,228, 4,211,562; 4,248,962; 4,259,437; 4,362, 878; 4,409,323; 4,477,563; 4,782,012; 4,962,018; 4,500, 634; 4,579,816; 4,607,004; 4,618,571; 4,678,739; 4,746, 600; 4,746,601; 4,791,049; 4,857,447; 4,865,959; 4,880, 342; 4,886,736; 4,937,179; 4,946,767; 4,948,716; 4,952, 485; 4,956,269; 4,959,299; 4,966,835; 4,985,336 as well as in patent publications GB 1,560,240; GB 2,007,662; GB 2,032,914; GB 2,099,167; DE 2,842,063, DE 2,937,127; DE 3,636,824; DE 3,644,416 as well as the following European Patent Publications: 272,573; 335,319; 336,411; 346, 899; 362, 870; 365,252; 365,346; 373,382; 376,212; 377,463; 378,236; 384,670; 396,486; 401,612; 401,613.

Such compounds are also disclosed in "Developer-Inhibitor-Releasing (DIR) Couplers for Color Photography," C. R. Barr, J. R. Thirtle and P. W. Vittum in *Photographic Science and Engineering*, Vol. 13, p. 174 (1969). Generally, the developer inhibitor-releasing (DIR) couplers include a coupler moiety and an inhibitor coupling-off moiety (IN). The inhibitor-releasing couplers may be of the time-delayed type (DIAR couplers) which also include a timing moiety or chemical switch which produces a delayed release of inhibitor. Examples of typical inhibitor moieties are: oxazoles, thiazoles, diazoles, triazoles, oxadiazoles, thiadiazoles, oxathiazoles, thiatriazoles, benzotriazoles, tetrazoles, benzimidazoles, indazoles, isoindazoles, mercaptotetrazoles, selenotetrazoles, mercaptobenzothiazoles, selenobenzothiazoles, mercaptobenzoxazoles, selenobenzoxazoles, mercaptobenzimidazoles, selenobenzimidazoles, benzodiazoles, mercaptooxazoles, mercaptothiadiazoles, mercaptothiazoles, mercaptotriazoles, mercaptooxadiazoles, mercaptodiazoles, mercaptooxathiazoles, telleurotetrazoles or benzisodiazoles. In a preferred embodiment, the inhibitor moiety or group is selected from the following formulas:

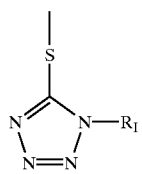 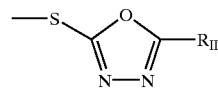

-continued

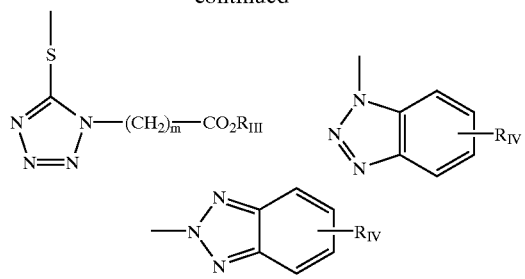

wherein $R_I$ is selected from the group consisting of straight and branched alkyls of from 1 to about 8 carbon atoms, benzyl, phenyl, and alkoxy groups and such groups containing none, one or more than one such substituent; $R_{II}$ is selected from $R_I$ and —$SR_I$; $R_{III}$ is a straight or branched alkyl group of from 1 to about 5 carbon atoms and m is from 1 to 3; and $R_{IV}$ is selected from the group consisting of hydrogen, halogens and alkoxy, phenyl and carbonamido groups, —$COOR_V$ and —$NHCOOR_V$ wherein $R_V$ is selected from substituted and unsubstituted alkyl and aryl groups.

Although it is typical that the coupler moiety included in the developer inhibitor-releasing coupler forms an image dye corresponding to the layer in which it is located, it may also form a different color as one associated with a different film layer. It may also be useful that the coupler moiety included in the developer inhibitor-releasing coupler forms colorless products and/or products that wash out of the photographic material during processing (so-called "universal" couplers).

A compound such as a coupler may release a PUG directly upon reaction of the compound during processing, or indirectly through a timing or linking group. A timing group produces the time-delayed release of the PUG such groups using an intramolecular nucleophilic substitution reaction (U.S. Pat. No. 4,248,962); groups utilizing an electron transfer reaction along a conjugated system (U.S. Pat. Nos. 4,409,323; 4,421,845; 4,861,701, Japanese Applications 57-188035; 58-98728, 58-209736; 58-209738); groups that function as a coupler or reducing agent after the coupler reaction (U.S. Pat. No. 4,438,193; U.S. Pat. No. 4,618,571) and groups that combine the features describe above. It is typical that the timing group is of one of the formulas:

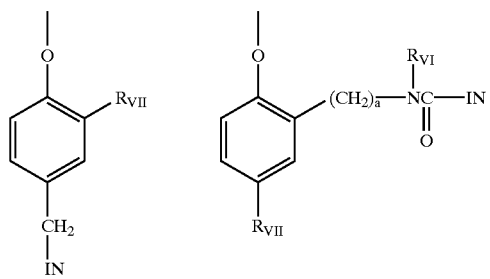

wherein IN is the inhibitor moiety, $R_{VII}$ is selected from the group consisting of nitro, cyano, alkylsulfonyl; sulfamoyl; and sulfonamido groups; a is 0 or 1; and $R_{VI}$ is selected from the group consisting of substituted and unsubstituted alkyl and phenyl groups. The oxygen atom of each timing group is bonded to the coupling-off position of the respective coupler moiety of the DIAR.

The timing or linking groups may also function by electron transfer down an unconjugated chain. Linking groups are known in the art under various names. Often they have been referred to as groups capable of utilizing a hemiacetal or iminoketal cleavage reaction or as groups capable of utilizing a cleavage reaction due to ester hydrolysis such as U.S. Pat. No. 4,546,073. This electron transfer down an unconjugated chain typically results in a relatively fast decomposition and the production of carbon dioxide, formaldehyde, or other low molecular weight by-products. The groups are exemplified in EP 464,612, EP 523,451, U.S. Pat. No. 4,146,396, Japanese Kokai 60-249148 and 60-249149.

Suitable developer inhibitor-releasing couplers for use in the present invention include, but are not limited to, the following:

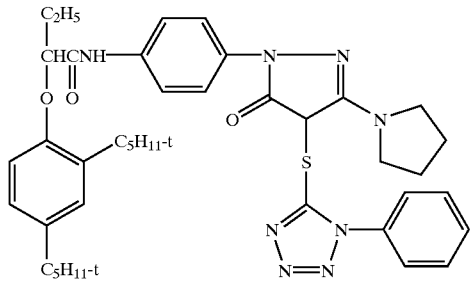

D1

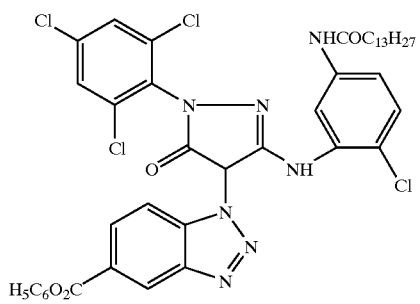

D2

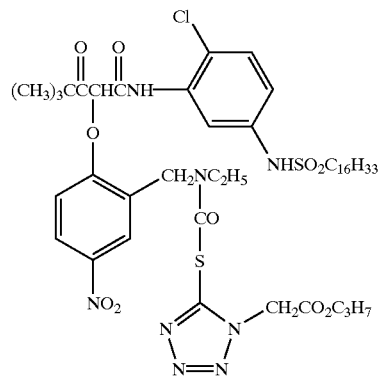

D3

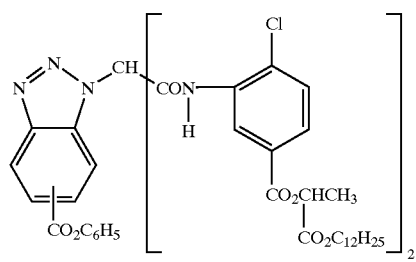

D4

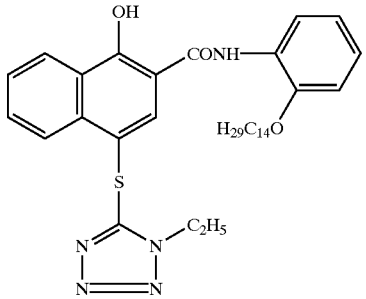

D5

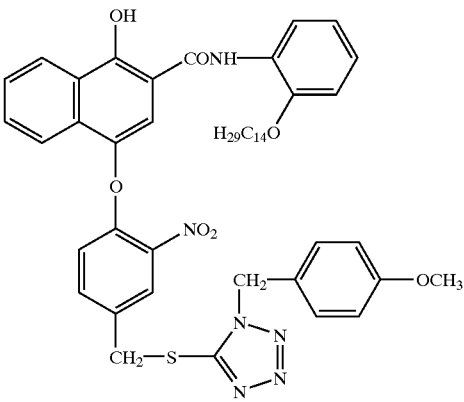

D6

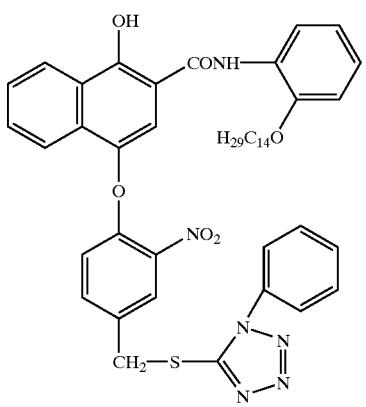

D7

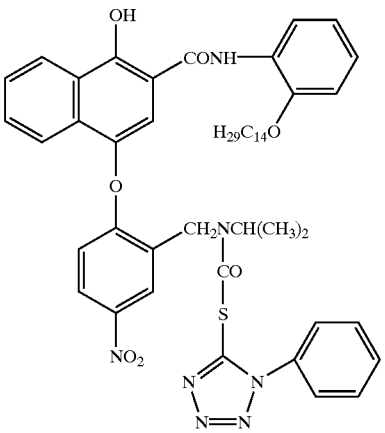

D8

-continued

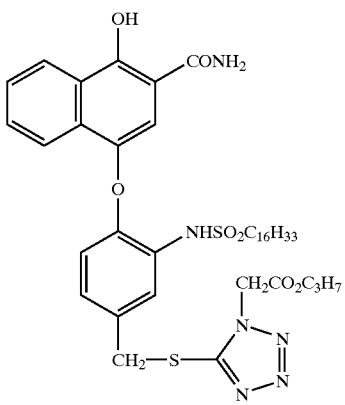

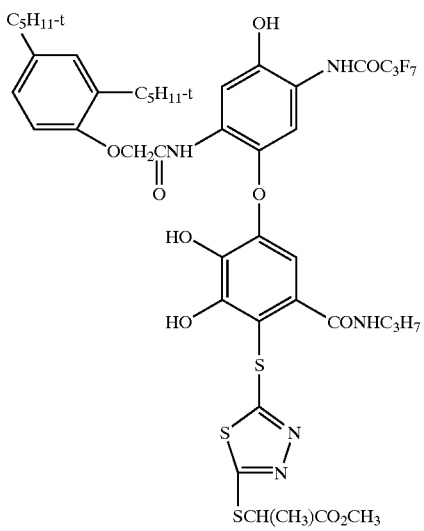

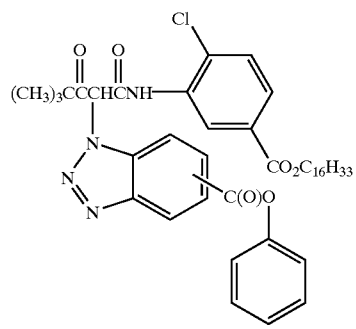

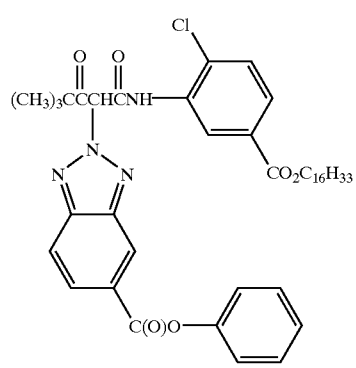

It is also contemplated that the present invention may be employed to obtain reflection color prints as described in *Research Disclosure*, November 1979, Item 18716, available from Kenneth Mason Publications, Ltd, Dudley Annex, 12a North Street, Emsworth, Hampshire P0101 7DQ, England. Materials useful in the invention may be coated on pH adjusted support as described in U.S. Pat. No. 4,917,994; on a support with reduced oxygen permeability (EP 553, 339); with epoxy solvents (EP 164,961); with nickel complex stabilizers (U.S. Pat. No. 4,346,165; U.S. Pat. No. 4,540,653 and U.S. Pat. No. 4,906,559 for example); with ballasted chelating agents such as those in U.S. Pat. No. 4,994,359 to reduce sensitivity to polyvalent cations such as calcium; and with stain reducing compounds such as described in U.S. Pat. No. 5,068,171. Other compounds useful in combination with the invention are disclosed in Japanese Published Applications described in Derwent Abstracts having accession numbers as follows: 90-072,629, 90-072,630; 90-072,631; 90-072,632; 90-072,633; 90-072, 634; 90-077,822; 90-078,229; 90-078,230; 90-079,336; 90-079,337; 90-079,338; 90-079,690; 90-079,691; 90-080, 487; 90-080,488; 90-080,489; 90-080,490; 90-080,491; 90-080,492; 90-080,494; 90-085,928; 90-086,669; 90-086, 670; 90-087,360; 90-087,361; 90-087,362; 90-087,363; 90-087,364; 90-088,097; 90-093,662; 90-093,663; 90-093, 664; 90-093,665; 90-093,666; 90-093,668; 90-094,055; 90-094,056; 90-103,409; 83-62,586; 83-09,959.

Conventional radiation-sensitive silver halide emulsions can be employed in the practice of this invention. Such emulsions are illustrated by *Research Disclosure*, Item 38755, September 1996, I. Emulsion grains and their preparation.

Useful in this invention are tabular grain silver halide emulsions. Tabular grains are those having two parallel major crystal faces and having an aspect ratio of at least 2. The term "aspect ratio" is the ratio of the equivalent circular diameter (ECD) of a grain major face divided by its thickness (t). Tabular grain emulsions are those in which the tabular grains account for at least 50 percent (preferably at least 70 percent and optimally at least 90 percent) of the total grain projected area. Preferred tabular grain emulsions are those in which the average thickness of the tabular grains is less than 0.3 micrometer (preferably thin—that is, less than 0.2 micrometer and most preferably ultrathin—that is, less than 0.07 micrometer). The major faces of the tabular grains can lie in either {111} or {100} crystal planes. The mean ECD of tabular grain emulsions rarely exceeds 10 micrometers and more typically is less than 5 micrometers.

In their most widely used form tabular grain emulsions are high bromide {111} tabular grain emulsions. Such emulsions are illustrated by Kofron et al U.S. Pat. No. 4,439,520, Wilgus et al U.S. Pat. No. 4,434,226, Solberg et al U.S. Pat. No. 4,433,048, Maskasky U.S. Pat. Nos. 4,435, 501, 4,463,087 and 4,173,320, Daubendiek et al U.S. Pat. Nos. 4,414,310 and 4,914,014, Sowinski et al U.S. Pat. No. 4,656,122, Piggin et al U.S. Pat. Nos. 5,061,616 and 5,061, 609, Tsaur et al U.S. Pat. Nos. 5,147,771, '772, '773, 5,171,659 and 5,252,453, Black et al U.S. Pat. Nos. 5,219, 720 and 5,334,495, Delton U.S. Pat. Nos. 5,310,644, 5,372, 927 and 5,460,934, Wen U.S. Pat. No. 5,470,698, Fenton et al U.S. Pat. No. 5,476,760, Eshelman et al U.S. Pat. Nos. 5,612,175 and 5,614,359, and Irving et al U.S. Pat. No. 5,667,954.

Ultrathin high bromide {111} tabular grain emulsions are illustrated by Daubendiek et al U.S. Pat. Nos. 4,672,027, 4,693,964, 5,494,789, 5,503,971 and 5,576,168, Antoniades et al U.S. Pat. No. 5,250,403, Olm et al U.S. Pat. No.

5,503,970, Deaton et al U.S. Pat. No. 5,582,965, and Maskasky U.S. Pat. No. 30 5,667,955.

High bromide {100} tabular grain emulsions are illustrated by Mignot U.S. Pat. Nos. 4,386,156 and 5,386,156.

High chloride {111} tabular grain emulsions are illustrated by Wey U.S. Pat. No. 4,399,215, Wey et al U.S. Pat. No. 4,414,306, Maskasky U.S. Pat. Nos. 4,400,463, 4,713,323, 5,061,617, 5,178,997, 5,183,732, 5,185,239, 5,399,478 and 5,411,852, and Maskasky et al U.S. Pat. Nos. 5,176,992 and 5,178,998. Ultrathin high chloride {111} tabular grain emulsions are illustrated by Maskasky U.S. Pat. Nos. 5,271,858 and 5,389,509.

High chloride {100} tabular grain emulsions are illustrated by Maskasky U.S. Pat. Nos. 5,264,337, 5,292,632, 5,275,930 and 5,399,477, House et al U.S. Pat. No. 5,320,938, Brust et al U.S. Pat. No. 5,314,798, Szajewski et al U.S. Pat. No. 5,356,764, Chang et al U.S. Pat. Nos. 5,413,904 and 5,663,041, Oyamada U.S. Pat. No. 5,593,821, Yamashita et al U.S. Pat. Nos. 5,641,620 and 5,652,088, Saitou et U.S. Pat. No. 5,652,089, and Oyamada et al U.S. Pat. No. 5,665,530. Ultrathin high chloride {100} tabular grain emulsions can be prepared by nucleation in the presence of iodide, following the teaching of House et al and Chang et al, cited above.

The emulsions can be surface-sensitive emulsions, i.e., emulsions that form latent images primarily on the surfaces of the silver halide grains, or the emulsions can form internal latent images predominantly in the interior of the silver halide grains. The emulsions can be negative-working emulsions, such as surface-sensitive emulsions or unfogged internal latent image-forming emulsions, or direct-positive emulsions of the unfogged, internal latent image-forming type, which are positive-working when development is conducted with uniform light exposure or in the presence of a nucleating agent. Tabular grain emulsions of the latter type are illustrated by Evans et al. U.S. Pat. No. 4,504,570.

Photographic elements can be exposed to actinic radiation, typically in the visible region of the spectrum, to form a latent image and can then be processed to form a visible dye image. Processing to form a visible dye image includes the step of contacting the element with a color-developing agent to reduce developable silver halide and oxidize the color-developing agent. Oxidized color developing agent in turn reacts with the coupler to yield a dye. If desired "Redox Amplification" as described in Research Disclosure XVIIIB(5) may be used.

A "color negative element" utilizes negative-working silver halide and provides a negative image upon processing. A first type of such element is a capture element; which is a color negative film that is designed for capturing an image in negative form rather than for viewing an image. A second type of such an element is a direct-view element that is designed, at least in part, for providing a positive image viewable by humans.

In the capture element, speed (the sensitivity of the element to low light conditions) is usually critical to obtaining sufficient image in such elements. Such elements are typically silver bromoiodide emulsions coated on a transparent support and are sold packaged with instructions to process in known color negative processes such as the Kodak C-41 process as described in The British Journal of Photography Annual of 1988, pages 191–198. If a color negative film element is to be subsequently employed to generate a viewable projection print as for a motion picture, a process such as the Kodak ECN-2 process described in the H-24 Manual available from Eastman Kodak Co. may be employed to provide the color negative image on a transparent support. Color negative development times are typically 3' 15" or less and desirably 90 or even 60 seconds or less.

A direct-view photographic element is one which yields a color image that is designed for human viewing (1) by reflected light, such as a photographic paper print, (2) by transmitted light, such as a display transparency, or (3) by projection, such as a color slide or a motion picture print. These direct-view elements may be exposed and processed in a variety of ways. For example, paper prints, display transparencies, and motion picture prints are typically produced by digitally printing or by optically printing an image from a color negative onto the direct-viewing element and processing though an appropriate negative-working photographic process to give a positive color image. The element may be sold packaged with instructions for digital printing or for processing using a color negative optical printing process, for example the Kodak RA-4 process, as generally described in PCT WO 87/04534 or U.S. Pat. No. 4,975,357, to form a positive image. Color projection prints may be processed, for example, in accordance with the Kodak ECP-2 process as described in the H-24 Manual. Color print development times are typically 90 seconds or less and desirably 45 or even 30 seconds or less. Color slides may be produced in a similar manner but are more typically produced by exposing the film directly in a camera and processing through a reversal color process or a direct positive process to give a positive color image. The foregoing images may also be produced by alternative processes such as digital printing.

Each of these types of photographic elements has its own particular requirements for dye hue, but in general they all require cyan dyes whose absorption bands are less deeply absorbing (that is, shifted away from the red end of the spectrum) than color negative films. This is because dyes in direct-view elements are selected to have the best appearance when viewed by human eyes, whereas the dyes in image capture materials are designed to best match the needs of the printing process.

A reversal element is capable of forming a positive image without optical printing. To provide a positive (or reversal) image, the color development step is preceded by development with a non-chromogenic developing agent to develop exposed silver halide, but not form dye, and followed by uniformly fogging the element to render unexposed silver halide developable. Such reversal elements are typically sold packaged with instructions to process using a color reversal process such as the Kodak E-6 process as described in The British Journal of Photography Annual of 1988, page 194. Alternatively, a direct positive emulsion can be employed to obtain a positive image.

The above elements are typically sold with instructions to process using the appropriate method such as the mentioned color negative (Kodak C-41), color print (Kodak RA-4), or reversal (Kodak E-6) process.

The photographic element of the invention can be incorporated into exposure structures intended for repeated use or exposure structures intended for limited use, variously referred to by names such as "single use cameras", "lens with film", or "photosensitive material package units".

Preferred color developing agents are p-phenylenediamines such as:
  4-amino-N,N-diethylaniline hydrochloride,
  4-amino-3-methyl-N,N-diethylaniline hydrochloride,
  4-amino-3-methyl-N-ethyl-N-(2-methanesulfonamidoethyl)aniline sesquisulfate hydrate, 4-amino-3-methyl-N-ethyl-N-(2-hydroxyethyl)aniline sulfate, 4-amino-3-(2-methanesulfonamidoethyl)-N,N-diethylaniline hydrochloride, and 4-amino-N-ethyl-N-(2-methoxyethyl)-m-toluidine di-p-toluene sulfonic acid.

Development is usually followed by the conventional steps of bleaching, fixing, or bleach-fixing, to remove silver or silver halide, washing, and drying.

EXAMPLES

In the following are described the preparation of two new intermediates of the invention (Examples 1 and 2) and their uses in the preparation of 2-eq phenolic cyan-dye forming couplers (Examples 3 and 4).

Example 1

6-(2-Dodecylsulfonylbutvryl)amino-5-fluoro-benzoxazol-2-one (Formula I; Y=F and R'=1-Dodecylsulfonylpropyl)

In a 500-ml flask, place 100 ml of concentrated nitric acid (70%) and warm to 45° C. Add 30.6 g (0.2 m) of 5-fluoro-benzoxazol-2-one (1a; X=F) and stir at 50° C. for 3 hrs. Add 240 ml of water slowly, and stir and cool to room temperature. Collect solid, wash with water, and dry in air to give 35.0 g (88%) of 5-fluoro-6-nitro-benzoxazol-2-one (2a; X=F) as pale yellow solids.

In a 250-ml flask, place 9.9 g (0.05 m) of 5-fluoro-6-nitro-benzoxazol-2-one (2a), 40 ml of isopropyl alcohol and 20 ml of propyl acetate, and 0.4 g 5% Pd/C with 1.5 ml of water. Add 16.8 g (0.2 m) of potassium formate in 20 ml of water, and stir the mixture vigorously at 55°–60° C. for 4 hrs. Keep strictly inert nitrogen atmosphere throughout the reaction. Take a TLC to confirm completeness of reaction. Cool the reaction mixture containing 6-amino-5-fluoro-benzoxazol-2-one (3a, X=F) to 40° C. under nitrogen, and add 40 ml of propyl acetate and a solution of 18.8 g (0.05 m×1.05 @95%) of 2-dodecylsulfonyl-butyryl chloride (R'COZ; R'=1-dodecylsulfonylpropyl and Z=Cl) in 60 ml of propyl acetate keeping the temperature at 40°–45° C. over 15 min. Stir the reaction mixture at 40° C. for 30 min. Add 60 ml of water and filter off catalyst and wash it with 60 ml of propyl acetate and 60 ml of water. Separate propyl acetate solution, wash with 120 ml of 1N HCl, and concentrate under a reduced pressure to a thick slurry. Cool the slurry in an ice-water bath for 2 hrs. Collect solid, wash with chilled propyl acetate and heptane, and dry in a vacuum oven to give 18.6 g (79%) of 6-(2-dodecylsulfonylbutyryl)amino-5-fluoro-benzoxazol-2-one (Formula I, Y=X=F and R'=1-dodecylsulfonylpropyl) as off-white solids.

Example 2

6-{2-(2,4-di-t-Pentylphenoxy)heptanoyl}amino-5-(4-t-butylphenoxy)-benzoxazol-2-one (Formula I; Y=4-t-Butylphenoxy and R'=1-(2,4-di-t-Pentylphenoxy)pentyl)

In a 250-ml flask, place 17.0 g (0.1 m) of chlorzoxazone (1b; X=Cl), 50 ml of acetic acid, and 0.14 g of sodium nitrite. Warm and stir the slurry to 50° C. Add 11.3 g (0.125 m) of concentrated nitric acid (70%) and stir the mixture at 55°–63° C. for 5 hrs. Add 100 ml of hot water, cool to room temperature and let it stand overnight. Collect solid, wash with water, and dry in air to give 18.7 g (87%) of 5-chloro-6-nitro-benzoxazol-2-one (2b; X=Cl) as pale yellow solids.

In a 250-ml flask, place 8.6 g (0.04 m) of 5-chloro-6-nitro-benzoxazol-2-one (2b, 1.3 g of tetrabutylammonium bromide, 11.1 g (0.08 m) of potassium carbonate powder, and 80 ml of acetone. Stir the mixture at 50° C. for 30 min. Add 7.4 g (0.04 m×1.08) of benzyl bromide. Stir the reaction mixture under reflux for 15 min. Distill off acetone, add 100 ml of water and 100 ml of toluene, stir for a few min. Separate toluene solution, wash with 100 ml of water, and concentrate under a reduced pressure to dryness to give 12.9 g (100%) of 3-N-benzyl-5-chloro-6-nitro-benzoxazol-2-one (4b; X=Cl) as a light brown oil.

In a 250-ml flask, place 7.8 g (0.04 m×1.3) of 4-t-butylphenol, 100 ml of toluene, 6 ml of N,N-dimethylacetamide, and 3.0 g (0.04 m×1.2 @90%) of KOH flakes. Heat the mixture under reflux with Dean-Stark trap to collect approximately 1.2 ml of water and 20 ml of toluene over 1 hr. Cool white slurry mixture to 90° C., and add 12.9 g (0.04 m) of 3-N-benzyl-5-chloro-6-nitro-benzoxazol-2-one (4b) and 0.3 g of tetrabutylammonium bromide. Heat under reflux for 1 hr. Addition of 0.3 g of phase transfer agent, tetrabutylammonium bromide, and heat under reflux for 1 hr period is repeated 3 more times. Cool the reaction mixture to 60° C., add 100 ml of hot water, and stir for a few min. Separate toluene solution, wash with 100 ml of 1N HCl, and concentrate under a reduced pressure to dryness to give 17.4 g (100%) of 3-N-benzyl-5-(4-t-butylphenoxy)-6-nitro-benzoxazol-2-one (5b; Y=4-t-butylphenoxy).

In a 500-ml flask, place 17.4 g (0.04 m) of 3-N-benzyl-5-(-t-butylphenoxy)-6-nitro-benzoxazol-2-one (5b), 70 ml of isopropyl alcohol and 35 ml of toluene. Heat the mixture to 60° C. Add 0.8 g of 5% Pd/C wet with 1 ml of water and 16.8 g (0.2 m) of potassium formate in 30 ml of water. Stir the reaction mixture vigorously at 60°–70° C. for 3 hrs under nitrogen. Cool the reaction mixture containing 6-amino-5-(4-t-butylphenoxy)-benzoxazol-2-one (6b; Y=4-t-butylphenoxy) to 15° C. and add 16.2 g (0.04 m×1.05 @95%) of 2-(2,4-di-t-pentylphenoxy)hexanoyl chloride (R'COZ; R'=1-(2,4-di-t-pentylphenoxy)pentyl and Z=Cl) in 60 ml of toluene slowly in drop wise over 1 hr period. Stir the mixture at 15° C. for another 30 min. Filter off catalyst and wash with a small volume of toluene and water. Separate toluene solution, wash with 100 ml of 1N HCl twice, and concentrate under a reduced pressure to a thick oil. Add 180 ml of heptane to the oil with gentle stirring. Cool in an ice-water bath for 1 hr. Collect solid, wash with heptane, and dry in a vacuum oven to give 18.1 g (72%) of 6-{2-(2,4-di-t-pentylphenoxy)hexanoyl}amino-5-(4-t-butylphenoxy)-benzoxazol-2-one (Formula I, Y=4-t-butylphenoxy and R'=1-(2,4-di-t-pentylphenoxy)pentyl).

Example 3

A 2-eq Phenolic Cyan Coupler 8a (Y=F, R'=1-Dodecylsulfonyl-propyl, and R"=3,4-dichlorophenylamino) from 6-(2-dodecylsulfonylbutyryl)-amino-5-fluoro-benzoxazol-2-one (Formula I; Y=F and R'=1-Dodecylsulfonyl-propyl)

In a 250-ml flask, place 8.47 g (0.018 m) of 6-(2-dodecylsulfonyl-butyryl)amino-5-fluoro-benzoxazol-2-one (Formula I) and 80 ml of xylene and heat to 85° C. Add 7 ml of ethylene glycol and 4.0 g of calcium hydroxide. Heat the mixture under reflux collecting approximately 4 ml of water and ethylene glycol and 20 ml of xylene in a Dean-Stark trap. Detach the trap and heat the reaction mixture under reflux (136°–137° C.) for 4 hrs. Cool to 100° C. and add 120 ml of propyl acetate and 120 ml of hot water.

Acidify the mixture with about 20 ml of acetic acid to pH 5.5 and add 1 g of sodium hydrosulfite and stir vigorously under nitrogen at 80° C. for 10 min. Separate propyl acetate-xylene solution, wash with water containing 1 g of sodium hydrosulfite under nitrogen, and concentrate under a reduced pressure to give a viscous oil. Dissolve the oil containing 4-(2-dodecyl-sulfonylbutyryl)amino-5-fluoro-2-hydroxyaniline (7a; Y=F and R'=1-dodecyl-sulfonylpropyl) in 100 ml of acetonitrile. Add a solution of 3.38 g (0.018 m) of 3,4-dichlophenyl isocyanate in 20 ml of acetonitrile and stir gently at room temperature overnight. Collect solid, wash with acetonitrile, and dry in a vacuum oven to give 9.1 g (80%) of the coupler 8a (Y=F, R'=1-dodecylsulfonylpropyl, and R"=3,4-dichlorophenylamino) as off-white solids.

Example 4

A 2-eq Phenolic Cyan Coupler 8b (Y=4-t-Butylphenoxy, R'=1-(2,4-di-t-Pentylphenoxy)pentyl, and R"=4-cyanophenylamino) from 6-{2-(2,4-di-t-Pentylphenoxy)hexanoyl}amino-5-(4-t-butylphenoxy)-benzoxazol-2-one (Formula I; Y=4-t-Butylphenoxy and R'=1-(2,4-di-t-Pentylphenoxy)pentyl)

In a 250-ml flask inert with nitrogen, place 11.3 g (0.018 m) of 6-{2-(2,4-di-t-pentylphenoxy)hexanoyl}amino-5-(4-t-butylphenoxy)-benzoxazol-2-one (Formula I), 120 ml of xylene, 12 ml of ethylene glycol, and 8.0 g of calcium hydroxide. Heat under reflux collecting approximately 7 ml of water-ethylene glycol and 20 ml of xylene in a Dean-Stark trap. Detach the trap and heat under reflux for 5 hrs. Cool to 80° C. and add 100 ml of toluene, 100 ml of hot water, 25 ml of acetic acid, and 2 g sodium hydrosulfite. Stir the mixture at 60°–65° C. for 15 min and filter through a Celite pad to remove interlayer insolubles. Separate toluene-xylene solution, wash with 100 ml of hot water+12 ml of acetic acid+2 g sodium hydrosulfite and 100 ml of hot water twice, and concentrate under a reduced pressure to a thick oil. Dissolve the oil in 200 ml of heptane, add seed crystals, and stand at room temperature over night. Cool in an ice-water bath for 1 hr, collect solid, wash with heptane, and dry in a vacuum oven to give 9.2 g (85%) of 2-amino-5-{2-(2,4-di-t-pentylphenoxy)hexanoyl}amino-4-(4-t-butylphenoxy)-phenol (7b; Y=4-t-butylphenoxy and R'=1-(2,4-di-t-pentylphenoxy)pentyl).

In a 250-ml flask inert with nitrogen, place 15.1 g (0.025 m) of 2-amino-5-{2-(2,4-di-t-pentylpbenoxy)hexanoyl}amino-4-(4-t-butylphenoxy)-phenol (7b), 6.0 g (0.025 m) of phenyl 4-cyanophenylaminocarbarmate (R"COZ; R"=4-cyano-phenylamino and Z=phenoxy), 1.7 g (0.025 m) of imidazole, and 75 ml of ethyl acetate. Heat the mixture under reflux for 5 hrs. Add 75 ml of hot water and 50 ml of 1N HCl and stir for a few min. Separate ethyl acetate solution, wash with 100 ml of warm water, and concentrate to a thick oil. Dissolve the oil in 50 ml of toluene, add 100 ml of heptane and seed crystals, and let it stand at room temperature over night. Cool in an ice-water bath for 1 hr, collect solid, wash with heptane and dry in a vacuum oven to give 15.9 g (85%) of the coupler 8b (Y=4-t-butylphenoxy, R'=1-(2,4-di-t-pentylphenoxy)pentyl, and R"=4-cyanophenyl-amino) as white solids.

The invention has been described in detail with particular reference to certain preferred embodiments thereof, but it will be understood that variations and modifications can be effected within the spirit and scope of the invention.

The entire contents of the patents and other publications referred to in this specification are incorporated herein by reference.

What is claimed is:

1. A method of making a 2-equivalent phenolic cyan-dye forming coupler from the compound of Formula I comprising the steps of:

(1) deblocking a compound of Formula I by hydrolysis of the benzoxazolone ring, and
    (2) N-acylating the deblocked compound to append an R"CO group to the amine at the 2-position,
        wherein Formula I is represented by the following:

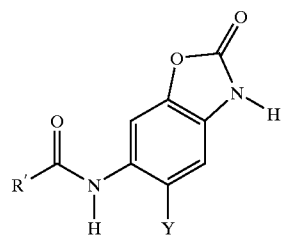

Formula I wherein

Y is halogen or a sustituent group linked to the rest of the compound by a hetero atom, R' is a group containing at least 8 carbon atoms; and R" is an alkyl, haloalkyl, aryl, heteroaryl, arylamino, or heteroarylamino group.

2. The method of claim 1 wherein R" is an aryl group optionally substituted by an alkyl, aryl, heteroaryl, halogen, cyano, alkoxycarbonyl, aryloxycarbonyl, alkylcarbonyl, arylcarbonyl, heteroarylcarbonyl, alkylsulfonyl, arylsulfonyl, or heteroarysulfonyl group.

3. The method of claim 1 wherein R" is a heteroaryl group optionally substituted by an alkyl, aryl, heterloaryl, halogen, cyano, alkoxycarbonyl, aryloxycarbonyl, alkylcarbonyl, arylcarbonyl, heteroarylcarbonyl, alkylsulfonyl, arylsulfonyl, or heteroarysulfonyl group.

4. The method of claim 1 wherein R" is an arylamino group optionally substituted by an alkyl, aryl, heteroaryl, halogen, cyano, alkoxycarbonyl, aryloxycarbonyl, alkylcarbonyl, arylcarbonyl, heteroarylcarbonyl, alkylsulfonyl, arylsulfonyl, or heteroarysulfonyl group.

5. The method of claim 1 wherein R" is a heteoarylamino group optionally substituted by an alkyl, heteroaryl, halogen, cyano, alkoxycarbonyl, arloxycarbonyl, alkylcarbonyl, arylcarbonyl, heteroarylcarbonyl, alkylsulfonyl, arylsulfoyl, or hetero-arysulfonyl group.

6. The method of claim 1 wherein the hydrolysis is carried out with a strong base in a high boiling organic solvent.

7. The method of claim 6 wherein the strong base is sodium hydroxide, potassium hydroxide, or calcium hydroxide in a toluene or xylene containing solvent.

8. The method of claim 1 wherein the hydrolysis is performed at a temperature of 100° C. to 200° C.

9. The method of claim 1 wherein the acylation is performed in an aprotic solvent.

10. The method of claim 1 wherein the aprotic solvent contains heptane, toluene, ethyl acetate, propyl acetate, or acetonitrile.

11. The method of claim 1 wherein the acylation is performed at a temperature of −10 to 40° C.

* * * * *

UNITED STATES PATENT AND TRADEMARK OFFICE
CERTIFICATE OF CORRECTION

PATENT NO.   : 6,515,176 B1
DATED        : February 4, 2003
INVENTOR(S)  : Chang-Kyu Kim It is certified that error appears in the above-identified patent and that said Letters Patent is hereby corrected as shown below:

Column 24,
Line 61, following "claim", delete "1" and insert -- 9 --.

Signed and Sealed this

Twenty-ninth Day of July, 2003

JAMES E. ROGAN
*Director of the United States Patent and Trademark Office*